United States Patent

Kawamura

[11] Patent Number: 6,077,953
[45] Date of Patent: Jun. 20, 2000

[54] 6-ALKOXYCARBONYLPYRIDAZIN-3-ONE COMPOUNDS

[75] Inventor: Shinichi Kawamura, Hyogo, Japan

[73] Assignee: Sumitomo Chemical Co., Ltd., Osaka, Japan

[21] Appl. No.: 09/328,505

[22] Filed: Jun. 9, 1999

[30] Foreign Application Priority Data

Jun. 11, 1998 [JP] Japan .................................. 10-163872

[51] Int. Cl.[7] .................................................. C07D 237/24
[52] U.S. Cl. ............................................. 544/239; 560/34
[58] Field of Search ............................................. 544/239

[56] References Cited

FOREIGN PATENT DOCUMENTS 19754348  6/1998  Germany .
97/07104  2/1997  WIPO .

OTHER PUBLICATIONS

Bestman et al, *Chemical Abstracts*, vol. 103, No. 22538 (1985).
*Pyridazines* by Raymond N. Castle (Editor), pp. 411 and 415 (1973).
Afaf Aly Nada et al., "The Utility of Phosphonium Ylides in Heterocyclic Synthesis: Synthesis of Pyridazinone and Tetrahydrocinnolinone Derivatives", *J. Chem. Research*, Synop. No. 7, 1997, pp. 236–237.
Richard H. Wiley et al., "2–Pyrones. XII. Gamma–Keto–-beta–methylglutaconic Anhydride Arylhydrazones and Their Conversion to 1–Aryl–3–carboxy–4–methyl–6–pyridazones", *Journal American Chemical Society*, vol. 77, 1955, pp. 403–405.
Himatkumar V. Patel et al., "Reaction of Triethyl Phosphonoacetate Anion With Phenylhydrazones: A New Method For The Preparation of 3(2H)–Pyridazinones", *Synthetic Communications*, vol. 21, No. 8–9, 1991, pp. 1021–1026.

*Primary Examiner*—Emily Bernhardt
*Attorney, Agent, or Firm*—Sughrue, Mion, Zinn, Macpeak & Seas, PLLC

[57] ABSTRACT

The 6-alkoxycarbonylpyridazin-3-one compounds given in the formula:

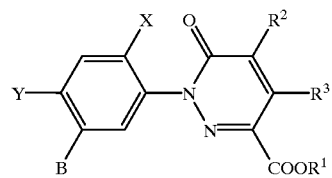

wherein, X represents a hydrogen and so on, Y represents a halogen atom, $R^1$ represents a $C_1$–$C_6$ alkyl group, $R^2$ represents a hydrogen and other groups as defind, $R^3$ represents a $C_1$–$C_3$ haloalkoxy group and B represents a hydrogen and other groups as defind, are intermediates to produce the pyridazin-3-one compounds given in the formula:

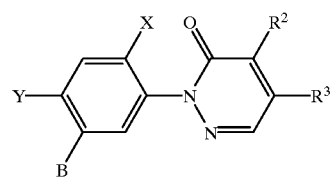

wherein X represents a hydrogen atom and other groups as defind, Y represents a halogen atom, $R^2$ represents a hydrogen atom and other groups as defind, $R^3$ represents a $C_1$–$C_3$ haloalkyl group and B represents a hydrogen atom and other groups as defined, which are herbicidal compounds.

5 Claims, No Drawings

6-ALKOXYCARBONYLPYRIDAZIN-3-ONE COMPOUNDS

FIELD OF THE INVENTION

The present invention relates to the 6-alkoxycarbonylpyridazin-3-one compounds of the formula (II) below and a method of producing the pyridazin-3-one compounds of the formula (I) below via said 6-alkoxycarbonylpyridazin-3-one compounds.

BACKGROUND ARTS

Hitherto, it has been known that the pyridazin-3-one compounds given in the formula (I):

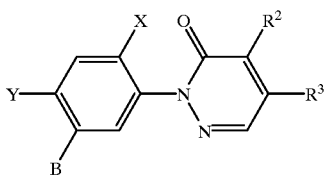

wherein, X represents a hydrogen or halogen atom; Y represents a halogen atom; $R^2$ represents a hydrogen atom or $C_1$–$C_3$ alkyl group; $R^3$ represents a $C_1$–$C_3$ haloalkyl group; B represents a hydrogen atom, $OR^4$ group or $COOR^5$ group; $R^4$ represents a hydrogen atom, $C_1$–$C_6$ alkyl, $C_3$–$C_6$ alkenyl, $C_3$–$C_6$ alkynyl, ($C_1$–$C_8$ alkoxy)carbonyl$C_1$–C6 alkyl or carboxy$C_1$–$C_6$ alkyl group; and $R^5$ represents a hydrogen atom, $C_1$–$C_6$ alkyl, $C_3$–$C_6$ alkenyl or $C_3$–$C_6$ alkynyl group, and their analogs have excellent herbicidal activity (WO 97/07104), and it has been demanded to develop a simple and convenient method to produce these pyridazin-3-one compounds.

SUMMARY OF THE INVENTION

The present invention serves intermediate compounds of the formula (II):

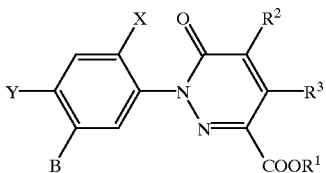

wherein, X, Y, B, $R^2$ and $R^3$ represent the same definitions as above and $R^1$ represents a $C_1$–$C_6$ alkyl group, in the case of producing the herbicidal pyridazin-3-one compounds given in the above formula (I). Further, the present invention serves a method of producing the pyridazin-3-one compounds given in the above formula (I). The method comprises i) reacting the hydrazone compound of the formula (III):

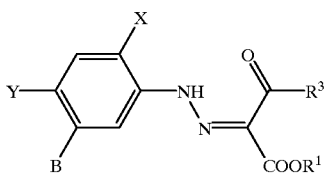

wherein, X, Y, B, $R^1$ and $R^3$ represent the same definitions as above, with the phosphorane compound given in the formula (IV):

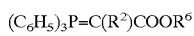

wherein, $R^2$ represents the same definition as above and $R^6$ represents a $C_1$–$C_6$ alkyl group, to obtain the 6-alkoxycarbonylpyridazin-3-one compounds of the formula (II) and ii) treating the obtained 6-alkoxycarbonylpyridazin-3-one compounds of the formula (II) with an acid.

DETAILED DESCRIPTION OF THE INVENTION

The present invention serves the 6-alkoxycarbonylpyridazin-3-one compounds given in the above formula (II) (hereinafter, the present compound(s)), which are useful as intermediates to produce the pyridazin-3-one compounds given in the formula (I).

In the present invention, examples of halogen atoms for X or Y include fluorine, chlorine and bromine atom; examples of $C_1$–$C_6$ alkyl group for $R^1$, $R^4$ or $R^5$ include methyl, ethyl, propyl, isopropyl, butyl, isobutyl, tert-butyl, amyl and isoamyl group; examples of $C_1$–$C_3$ alkyl group for $R^2$ include methyl and ethyl group; examples of $C_1$–$C_3$ haloalkyl group for $R^3$ include trifluoromethyl and pentafluoroethyl group; examples of $C_3$–$C_6$ alkenyl group for $R^4$ or $R^5$ include allyl, 1-methyl-2-propenyl, 3-butenyl, 2-butenyl, 3-methyl-2-butenyl and 2-methyl-3-butenyl group; examples of $C_3$–$C_6$ alkynyl group for $R^4$ or $R^5$ include propargyl, 1-methyl-2-propynyl, 2-butynyl and 1,1-dimethyl-2-propynyl group; examples of ($C_1$–$C_8$ alkoxy) carbonyl$C_1$–$C_6$ alkyl group for $R^4$ include methoxycarbonylmethyl, ethoxycarbonylmethyl, propoxycarbonylmethyl, isopropoxycarbonylmethyl, butoxycarbonylmethyl, isobutoxycarbonylmethyl, tert-butoxycarbonylmethyl, amyloxycarbonylmethyl, isoamyloxycarbonylmethyl, tert-amyloxycarbonylmethyl, 1-methoxycarbonylethyl, 1-ethoxycarbonylethyl, 1-propoxycarbonylethyl, 1-isopropoxycarbonylethyl,1-butoxycarbonylethyl, 1-isobutoxycarbonylethyl, 1-tert-butoxycarbonylethyl, 1-amyloxycarbonylethyl 1-isoamyloxycarbonylethyl and 1-(tert-amyloxycarbonyl) ethyl group; and examples of carboxy$C_1$–$C_6$ alkyl group for $R^4$ include carboxymethyl, 1-carboxyethyl and 2-carboxyethyl group.

The following explains a method to prepare the present compounds (hereinafter referred as process 1). The present compounds can be produced by reacting the hydrazone compound of the formula (III) with the phosphorane compound of the formula (IV).

Examples of $C_1$–$C_6$ alkyl group for $R^6$ include methyl, ethyl, propyl, butyl and amyl group.

Said reaction is usually performed in a solvent. The range of the reaction temperature is usually from −20 to 150° C., preferably from 20 to 130° C. And the range of the reaction time is usually instantaneous to 72 hours.

The amount of the reactants cooperating in the reaction is theoretically the rate of 1 mole of the phosphorane compound given in the formula (IV), per 1 mole of the hydrazone compound given in the formula (III), but the rate may be optionally varied according to the reaction condition.

Suitable solvents include, for example, aliphatic or alicyclic hydrocarbons such as hexane, heptane, octane, nonane, decane, ligroin, cyclohexane and petroleum ether; aromatic hydrocarbons such as benzene, toluene, xylene and mesitylene; halogenated aromatic hydrocarbons such as monochlorobenzene, dichlorobenzene and benzotrifluoride; ethers such as diethyl ether, diisopropyl ether, 1,4-dioxane, tetrahydrofuran, ethyleneglycol dimethyl ether and methyl t-butyl ether; nitro compounds such as nitromethane and nitrobenzene; acid amides such as formamide, N,N-dimethylformamide and acetamide; tertiary amines such as pyridine, triethylamine, diisopropylethylamine, tributylamine, N,N-dimethylaniline, N,N-diethylaniline and N-methylmorpholine; sulfur-containing compounds such as dimethylsulfoxide and sulfolan; alcohols such as methanol, ethanol, propanol, 2-propanol, butanol, tert-butyl alcohol, amyl alcohol, isoamyl alcohol and tert-amyl alcohol; water; and mixtures thereof.

The reaction mixture after the reaction is subjected to work-up procedure such as evaporating solvent and progressing to chromatography operations, or concentration after the reaction mixture is poured into water, extracted with an organic solvent, and when necessary, the obtained product may be purified by chromatography or recrystallization to isolate the objective present compounds.

The preparation method of the starting material for the present compound is explained below.

The phosphorane compound given in the formula (IV) is on the market and is also prepared according to the method given in Zikken Kagaku Koza, 4th ed., vol. 24, pp 259–260 Maruzen k.k.).

The hydrazone compound given in the formula (IV) can be produced by converting the aniline compound given in the formula (V):

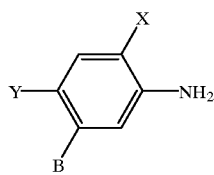

wherein X, Y and B represent the same definitions as above, into a diazonium salt by usual method such as reaction with nitrite (e.g. sodium nitrite) or nitrous acid in acidic aqueous solution, and then reacting the diazonium salt with an acetoacetate ester derivative given in the formula (VI):

wherein $R^1$ and $R^3$ represent the same definitions as above (cf. WO 97/07104).

The following explains a method to produce the pyridazin-3-one compounds given in the formula (I) by treating the present compound with an acid (hereinafter referred as process 2).

Said reaction is performed within a solvent. The range of the reaction time is usually from instantaneous to 240 hours, preferably 1 to 120 hours, and the range of the reaction temperature is usually from room temperature to 250° C., preferably 50 to 200° C.

The amount of the reactant that cooperates in the reaction is the rate of a catalytic amount to excess of the acid per 1 mole of the 6-alkoxycarbonylpyridazin-3-one compound given in the formula (II).

As the acid that cooperates in the reaction, inorganic acids such as sulfuric acid and hydrochloric acid; organic acids such as p-toluenesulfonic acid, methanesulfonic acid, trifluoromethanesulfonic acid and trifluoroacetic acid; and the like are exemplified.

As the solvent, water or a mixture of water and the other solvent is utilized.

Examples of the solvents utilized by mixing with water include aliphatic or alicyclic hydrocarbons such as hexane, heptane, nonane, decane, ligroin, cyclohexane and petroleum ether; aromatic hydrocarbons such as benzene, toluene, xylene and mesitylene; halogenated aromatic hydrocarbons such as monochlorobenzene, dichlorobenzene and benzotrifluoride; ethers such as diethyl ether, diisopropyl ether, 1,4-dioxane, tetrahydrofuran, ethyleneglycol dimethyl ether and methyl t-butyl ether; alcohols such as methanol, ethanol, propanol, 2-propanol, butanol, tert-butyl alcohol, amyl alcohol, isoamyl alcohol and tert-amyl alcohol; nitro compounds such as nitromethane and nitrobenzene; sulfur-containing compounds such as dimethyl sulfoxide and sulfolane; carboxylic acids such as formic acid, acetic acid and propionic acid; and mixtures thereof.

In case that sulfuric acid is utilized as an acid, it is preferable that about 10% by weight to 90% by weight of water based on sulfuric acid exists in the reaction mixture.

The reaction mixture after the reaction subjected to work-up procedures to give the objective products, for example, the reaction mixture is poured into water, extracted with an organic solvent, the organic layer is dried and then concentrated, or the reaction mixture is poured into water, the precipitated crystals are filtered off, washed with water and then dried. If necessary, the obtained product may be further purified by chromatography or recrystallization procedure.

In process 2, the pyridazin-3-one compound given in the formula (I), wherein a substituent on its benzene ring is converted, may be by-produced on a certain reaction condition when conversion to 6-unsubstituted pyridazine. Even in that case, the substituent of the product can be easily converted to the substituent on the benzene ring prior to process 2 by known methods (cf. WO 97/07104). Typical examples are shown below.

(1) The pyridazin-3-one compound given in the formula (I), wherein B represents $OR^4$ group and $R^4$ is a hydrogen atom, may be produced on a certain reaction condition, when the present compound wherein B represents $OR^4$ group and $R^4$ is a $C_1$–$C_6$ alkyl, $C_3$–$C_6$ alkenyl, $C_3$–$C_6$ alkynyl, ($C_1$–$C_8$ alkoxy)carbonyl $C_1$–$C_6$ alkyl or carboxy $C_1$–$C_6$ alkyl group is subjected to process 2. The obtained compound can be converted to the pyridazin-3-one compound given in the formula (I), wherein B represents $OR^4$ group and $R^4$ is a $C_1$–$C_6$ alkyl, $C_3$–$C_6$ alkenyl, $C_3$–$C_6$ alkynyl, ($C_1$–$C_8$ alkoxy)carbonyl $C_1$–$C_6$ alkyl or carboxy $C_1$–$C_6$ alkyl group by known methods.

(2) The pyridazin-3-one compound given in the formula (I), wherein B represents $OR^4$ group and $R^4$ is a carboxy $C_1$–$C_6$ alkyl group, may be produced on a certain reaction condition, when the present compound wherein B represents $OR^4$ group and $R^4$ is a ($C_1$–$C_8$ alkoxy)carbonyl $C_1$–$C_6$ alkyl group is subjected to process 2. The obtained compound can be converted to the pyridazin-3-one compound given in the formula (I), wherein B represents $OR^4$ group and $R^4$ is a ($C_1$–$C_8$ alkoxy)carbonyl $C_1$–$C_6$ alkyl group by known methods.

(3) The pyridazin-3-one compound given in the formula (I), wherein B represents COOR$^5$ group and R$^5$ is a hydrogen atom, may be produced on a certain reaction condition, when the present compound wherein B represents COOR$^3$ group and R$^5$ is a C$_1$–C$_6$ alkyl, C$_3$–C$_6$ alkenyl or C$_3$–C$_6$ alkynyl group is subjected to process 2. The obtained compound can be converted to the pyridazin-3-one compound given in the formula (I), wherein B represents COOR$^5$ group and R$^5$ is a C$_1$–C$_6$ alkyl, C$_3$–C$_6$ alkenyl or C$_3$–C$_6$ alkynyl group by known methods.

EXAMPLES

Subsequently, the examples describe the present invention in detail. The present invention is not limited to the following examples. The compound numbers in the examples are the numbers in Tables 1 to 6 below.

The production examples of the present compounds are below.

Production Example 1-1

3.22 g of Compound 2-16 and 4.18 g of (carbethoxymethylene) triphenylphosphorane [(C$_6$H$_5$)$_3$P=CHCOOC$_2$H$_5$] were dissolved into 50 ml of toluene and refluxed for 6.5 hours under heating. The solvent was removed under reduced pressure and the residue was subjected to silica gel column chromatography (eluent: hexane/ethyl acetate=4/1), and then the obtained crystals were washed with hexane to afford 1.27 g of 2-(4-chlorophenyl)-6-ethoxycarbonyl-5-trifluoromethylpyridazin-3-one, the present compound 1-51 (yield 37%).

$^1$H-NMR (CDCl$_3$/1250 MHz); 1.40(3H,t), 4.44(2H,q), 7.41(1H,s), 7.47(2H,d), 7.63(2H,d)

Production Example 1-2

3.99 g of Compound 2-4 and 3.99 g of (carbethoxyethylidene) triphenylphosphorane [(C$_6$H$_5$)$_3$P=C(CH$_3$)COOC$_2$H$_5$] were dissolved into 50 ml of toluene and refluxed for 10 hours under heating. The solvent was removed under reduced pressure and the residue was subjected to silica gel column chromatography (eluent: hexane/ethyl acetate=9/1) to afford 2.63 g of 2-(4-chloro-2-fluoro-5-isopropoxyphenyl)-6-ethoxycarbonyl-4-methyl-5-trifluoromethylpyridazin-3-one, the present compound 1-31 (yield 60%).

$^1$H-NMR (CDCl$_3$/250 MHz); 1.35–1.41(9H,m), 2.48(3H, q), 4.35–4.55(3H,m), 6.98(1H,d), 7.29(1H,d)

Production Example 1-3

One gram (1.0 g) of 2-(4-chloro-2-fluoro-5-isopropoxyphenyl)-6-ethoxycarbonyl-4-methyl-5-trifluoromethylpyridazin-3-one and 1.0 g of sulfuric acid are mixed at room temperature, and stirred for 30 minutes. The reaction mixture was poured into water and extracted with 100 ml of ethyl acetate. The organic layer was washed with 50 ml of water 3 times and dried over anhydrous magnesium sulfate. The solvent was removed under reduced pressure and the obtained crystals was washed with 50 ml of n-hexane to afford 0.78 g of 2-(4-chloro-2-fluoro-5-hydroxyphenyl)-6-ethoxycarbonyl-4-methyl-5-trifluoromethylpyridazin-3-one, the present compound 1-27 (yield 87%).

$^1$H-NMR (CDCl$_3$/300 MHz); 1.38(3H,t), 2.49(3H,q), 4.41(2H,q), 5.72(1H,br), 7.08(1H,d), 7.25(1H,d)

Production Example 1-4

12.5 g of Compound 2-18 and 12.19 g of (carbethoxyethylidene) triphenylphosphorane [(C$_6$H$_5$)$_3$P=C(CH$_3$)COOC$_2$H$_5$] were dissolved into 100 ml of toluene and refluxed for 5 hours under heating. The solvent was removed under reduced pressure and the residue was subjected to silica gel column chromatography (eluent: hexane/ethyl acetate=9/1) to afford 7.5 g of 2-(4-chloro-3-isopropoxycarbonylphenyl)-6-ethoxycarbonyl-4-methyl-5-trifluoromethylpyridazin-3-one, the present compound 1-109 (yield 55%).

$^1$H-NMR (CDCl$_3$/300 MHz); 1.35–1.43(9H,m), 2.48(3H, q), 4.42(2H,q), 5.20–5.35(1H,m), 7.55(1H,d), 7.69(1H,dd), 8.08(1H,d)

Typical examples of the present compounds are given in Tables 1 to 4 with their compound numbers. The present compounds are not limited to the following examples.

The compounds given in the formula (VI):

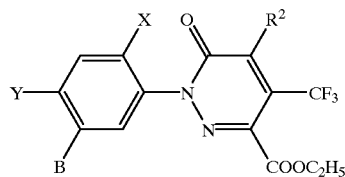

TABLE 1

| Compound Nos. | R$^2$ | X | Y | B |
|---|---|---|---|---|
| 1-1 | H | F | Cl | H |
| 1-2 | H | F | Cl | OH |
| 1-3 | H | F | Cl | OCH$_3$ |
| 1-4 | H | F | Cl | OC$_2$H$_5$ |
| 1-5 | H | F | Cl | OC$_3$H$_7$ |
| 1-6 | H | F | Cl | OCH(CH$_3$)$_2$ |
| 1-7 | H | F | Cl | OC$_4$H$_9$ |
| 1-8 | H | F | Cl | OCH$_2$CH(CH$_3$)$_2$ |
| 1-9 | H | F | Cl | OC(CH$_3$)$_3$ |
| 1-10 | H | F | Cl | OCH$_2$CH=CH$_2$ |
| 1-11 | H | F | Cl | OCH(CH$_3$)CH=CH$_2$ |
| 1-12 | H | F | Cl | OCH$_2$C(CH$_3$)=CH$_2$ |
| 1-13 | H | F | Cl | OCH$_2$C≡CH |
| 1-14 | H | F | Cl | OCH(CH$_3$)C≡CH |
| 1-15 | H | F | Cl | OCH$_2$COOCH$_3$ |
| 1-16 | H | F | Cl | OCH$_2$COOC$_2$H$_5$ |
| 1-17 | H | F | Cl | OCH$_2$COOC$_3$H$_7$ |
| 1-18 | H | F | Cl | OCH$_2$COOCH(CH$_3$)$_2$ |
| 1-19 | H | F | Cl | OCH$_2$COOC$_5$H$_{11}$ |
| 1-20 | H | F | Cl | OCH(CH$_3$)COOCH$_3$ |
| 1-21 | H | F | Cl | OCH(CH$_3$)COOC$_2$H$_5$ |
| 1-22 | H | F | Cl | OCH(CH$_3$)COOCH(CH$_3$)$_2$ |
| 1-23 | H | F | Cl | OCH(CH$_3$)COOC$_5$H$_{11}$ |
| 1-24 | H | F | Cl | OCH$_2$COOH |
| 1-25 | H | F | Cl | OCH(CH$_3$)COOH |
| 1-26 | CH$_3$ | F | Cl | H |
| 1-27 | CH$_3$ | F | Cl | OH |
| 1-28 | CH$_3$ | F | Cl | OCH$_3$ |
| 1-29 | CH$_3$ | F | Cl | OC$_2$H$_5$ |
| 1-30 | CH$_3$ | F | Cl | OC$_3$H$_7$ |

TABLE 2

| Compound Nos. | R$^2$ | X | Y | B |
|---|---|---|---|---|
| 1-31 | CH$_3$ | F | Cl | OCH(CH$_3$)$_2$ |
| 1-32 | CH$_3$ | F | Cl | OC$_4$H$_9$ |
| 1-33 | CH$_3$ | F | Cl | OCH$_2$CH(CH$_3$)$_2$ |
| 1-34 | CH$_3$ | F | Cl | OC(CH$_3$)$_3$ |
| 1-35 | CH$_3$ | F | Cl | OCH$_2$CH=CH$_2$ |
| 1-36 | CH$_3$ | F | Cl | OCH(CH$_3$)CH=CH$_2$ |
| 1-37 | CH$_3$ | F | Cl | OCH$_2$C(CH$_3$)=CH$_2$ |
| 1-38 | CH$_3$ | F | Cl | OCH$_2$C≡CH |
| 1-39 | CH$_3$ | F | Cl | OCH(CH$_3$)C≡CH |
| 1-40 | CH$_3$ | F | Cl | OCH$_2$COOCH$_3$ |
| 1-41 | CH$_3$ | F | Cl | OCH$_2$COOC$_2$H$_5$ |
| 1-42 | CH$_3$ | F | Cl | OCH$_2$COOC$_4$H$_7$ |
| 1-43 | CH$_3$ | F | Cl | OCH$_2$COOCH(CH$_3$)$_2$ |
| 1-44 | CH$_3$ | F | Cl | OCH$_2$COOC$_5$H$_{11}$ |

TABLE 2-continued

| Compound Nos. | R² | X | Y | B |
|---|---|---|---|---|
| 1-45 | CH₃ | F | Cl | OCH(CH₃)COOCH₃ |
| 1-46 | CH₃ | F | Cl | OCH(CH₃)COOC₂H₅ |
| 1-47 | CH₃ | F | Cl | OCH(CH₃)COOCH(CH₃)₂ |
| 1-48 | CH₃ | F | Cl | OCH(CH₃)COOC₅H₁₁ |
| 1-49 | CH₃ | F | Cl | OCH₂COOH |
| 1-50 | CH₃ | F | Cl | OCH(CH₃)COOH |
| 1-51 | H | H | Cl | H |
| 1-52 | H | H | Cl | OH |
| 1-53 | H | H | Cl | OCH₃ |
| 1-54 | H | H | Cl | OC₂H₅ |
| 1-55 | H | H | Cl | OC₄H₇ |
| 1-56 | H | H | Cl | OCH(CH₃)₂ |
| 1-57 | H | H | Cl | OC₄H₉ |
| 1-58 | H | H | Cl | OCH₂CH(CH₃)₂ |
| 1-59 | H | H | Cl | OC(CH₃)₃ |
| 1-60 | H | H | Cl | OCH₂CH=CH₂ |
| 1-61 | H | H | Cl | OCH(CH₃)CH=CH₂ |
| 1-62 | H | H | Cl | OCH₂C(CH₃)=CH₂ |
| 1-63 | H | H | Cl | OCH₂C≡CH |
| 1-64 | H | H | Cl | OCH(CH₃)C≡CH |
| 1-65 | H | H | Cl | OCH₂COOCH₃ |

TABLE 3

| Compound Nos. | R² | X | Y | B |
|---|---|---|---|---|
| 1-66 | H | H | Cl | OCH₂COOC₂H₅ |
| 1-67 | H | H | Cl | OCH₂COOC₄H₇ |
| 1-68 | H | H | Cl | OCH₂COOCH(CH₃)₂ |
| 1-69 | H | H | Cl | OCH₂COOC₅H₁₁ |
| 1-70 | H | H | Cl | OCH(CH₃)COOCH₃ |
| 1-71 | H | H | Cl | OCH(CH₃)COOC₂H₅ |
| 1-72 | H | H | Cl | OCH(CH₃)COOCH(CH₃)₂ |
| 1-73 | H | H | Cl | OCH(CH₃)COOC₅H₁₁ |
| 1-74 | H | H | Cl | OCH₂COOH |
| 1-75 | H | H | Cl | OCH(CH₃)COOH |
| 1-76 | CH₃ | H | Cl | H |
| 1-77 | CH₃ | H | Cl | OH |
| 1-78 | CH₃ | H | Cl | OCH₃ |
| 1-79 | CH₃ | H | Cl | OC₂H₅ |
| 1-80 | CH₃ | H | Cl | OC₄H₇ |
| 1-81 | CH₃ | H | Cl | OCH(CH₃)₂ |
| 1-82 | CH₃ | H | Cl | OC₄H₉ |
| 1-83 | CH₃ | H | Cl | OCH₂CH(CH₃)₂ |
| 1-84 | CH₃ | H | Cl | OC(CH₃)₃ |
| 1-85 | CH₃ | H | Cl | OCH₂CH=CH₂ |
| 1-86 | CH₃ | H | Cl | OCH(CH₃)CH=CH₂ |
| 1-87 | CH₃ | H | Cl | OCH₂C(CH₃)=CH₂ |
| 1-88 | CH₃ | H | Cl | OCH₂C≡CH |
| 1-89 | CH₃ | H | Cl | OCH(CH₃)C≡CH |
| 1-90 | CH₃ | H | Cl | OCH₂COOCH₃ |
| 1-91 | CH₃ | H | Cl | OCH₂COOC₂H₅ |
| 1-92 | CH₃ | H | Cl | OCH₂COOC₄H₇ |
| 1-93 | CH₃ | H | Cl | OCH₂COOCH(CH₃)₂ |
| 1-94 | CH₃ | H | Cl | OCH₂COOC₅H₁₁ |
| 1-95 | CH₃ | H | Cl | OCH(CH₃)COOCH₃ |
| 1-96 | CH₃ | H | Cl | OCH(CH₃)COOC₂H₅ |
| 1-97 | CH₃ | H | Cl | OCH(CH₃)COOCH(CH₃)₂ |
| 1-98 | CH₃ | H | Cl | OCH(CH₃)COOC₅H₁₁ |
| 1-99 | CH₃ | H | Cl | OCH₂COOH |
| 1-100 | CH₃ | H | Cl | OCH(CH₃)COOH |

TABLE 4

| Compound Nos. | R² | X | Y | B |
|---|---|---|---|---|
| 1-101 | H | H | Cl | COOH |
| 1-102 | H | H | Cl | COOCH₃ |
| 1-103 | H | H | Cl | COOC₂H₅ |
| 1-104 | H | H | Cl | COOCH(CH₃)₂ |
| 1-105 | H | H | Cl | COOCH₂CH=CH₂ |
| 1-106 | CH₃ | H | Cl | COOH |

TABLE 4-continued

| Compound Nos. | R² | X | Y | B |
|---|---|---|---|---|
| 1-107 | CH₃ | H | Cl | COOCH₃ |
| 1-108 | CH₃ | H | Cl | COOC₂H₅ |
| 1-109 | CH₃ | H | Cl | COOCH(CH₃)₂ |
| 1-110 | CH₃ | H | Cl | COOCH₂CH=CH₂ |
| 1-111 | H | F | Cl | COOH |
| 1-112 | H | F | Cl | COOCH₃ |
| 1-113 | H | F | Cl | COOC₂H₅ |
| 1-114 | H | F | Cl | COOCH(CH₃)₂ |
| 1-115 | H | F | Cl | COOCH₂CH=CH₂ |
| 1-116 | CH₃ | F | Cl | COOH |
| 1-117 | CH₃ | F | Cl | COOCH₃ |
| 1-118 | CH₃ | F | Cl | COOC₂H₅ |
| 1-119 | CH₃ | F | Cl | COOCH(CH₃)₂ |
| 1-120 | CH₃ | F | Cl | COOCH₂CH=CH₂ |
| 1-121 | CH₃ | H | Br | H |
| 1-122 | CH₃ | F | Br | H |
| 1-123 | CH₃ | F | Br | OH |
| 1-124 | CH₃ | F | Br | OCH(CH₃)₂ |
| 1-125 | CH₃ | Cl | Cl | H |

The production examples of the hydrazone compounds given in the formula (III) are described as reference examples 1 below.

Reference Example 1-1

A mixture of 6.38 g of 4-chloroaniline and 30 ml of conc. hydrochloric acid (35–37% by weight) was heated at 50° C. for 55 minutes. After cooling the reaction solution to 0° C., a solution consisting of 3.62 g of sodium nitrite and 10 ml of water was added to the above reaction solution at 0° C. and stirred for 2 hours at the same temperature to give a diazonium salt solution.

Separately, 35 g of sodium acetate, 50 ml of water and 9.66 g of ethyl 3,3,3-trifluoroacetoacetate were charged into a flask, mixed and cooled to 0° C. To the obtained solution, the above diazonium salt solution was added over a period of 15 minutes at 0° C. The reaction solution was brought to room temperature and stirred for 55 minutes. The precipitated crystals were filtered off, washed with water and dried under reduced pressure at 50° C. to afford 15.23 g of the present compound 2-16 (yield 95%).

Reference Example 1-2

To 60 ml of conc. hydrochloric acid (35–37% by weight) cooled to 0° C., 10.69 g of isopropyl 5-amino-2-chlorobenzoate was added, brought to room temperature and stirred for 30 minutes. After cooling the reaction mixture to 0° C., a solution consisting of 3.62 g of sodium nitrite and 10 ml of water was added to the reaction mixture over a period of 5 minutes at 0° C. and the mixture was stilled for 30 minutes at 0° C. to give a diazonium salt solution. Separately, 70 g of sodium acetate, 100 ml of water and 9.21 g of ethyl 3,3,3-trifluoroacetoacetate were charged into a flask, mixed and cooled to 0° C. To the obtained solution, the above diazonium salt solution was added over a period of 10 minutes at 0° C. and stirred for 1 hour at 0° C. The reaction solution was poured into water and extracted with 500 ml of ethyl acetate. The organic layer was washed with 500 ml of water twice and dried over anhydrous magnesium sulfate. The solvent was removed under reduced pressure and the residue was subjected to silica gel column chromatography (hexane: ethyl acetate=9:1-3:1) to afford 13.13 g of the present compound 2-18 (yield 64%).

$^1$H-NMR (CDCl₃/300 MHz); 1.40–1.45(9H,m), 4.42(2H, q), 5.29(1H,m), 7.45–7.55(2H,m), 7.83(1H,d)

Examples of the hydrazone compounds given in the formula (III) are given in Table 5 with their compound numbers.

TABLE 5

The compounds given in the formula:

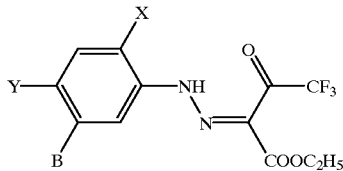

| Compound Nos. | X | Y | B |
|---|---|---|---|
| 2-1 | F | Cl | H |
| 2-2 | F | Cl | OH |
| 2-3 | F | Cl | $OCH_3$ |
| 2-4 | F | Cl | $OCH(CH_3)_2$ |
| 2-5 | F | Cl | $OCH_2C\equiv CH$ |
| 2-6 | F | Cl | $OCH(CH_3)C\equiv CH$ |
| 2-7 | F | Cl | $OCH_2COOH$ |
| 2-8 | F | Cl | $OCH_2COOCH_3$ |
| 2-9 | F | Cl | $OCH_2COOC_2H_5$ |
| 2-10 | F | Cl | $OCH(CH_3)COOCH_3$ |
| 2-11 | F | Cl | $OCH(CH_3)COOC_2H_5$ |
| 2-12 | F | Cl | $COOH$ |
| 2-13 | F | Cl | $COOCH_3$ |
| 2-14 | F | Cl | $COOC_2H_5$ |
| 2-15 | F | Cl | $COOCH(CH_3)_2$ |
| 2-16 | H | Cl | H |
| 2-17 | H | Cl | $OCH(CH_3)_2$ |
| 2-18 | H | Cl | $COOCH(CH_3)_2$ |
| 2-19 | F | Br | H |
| 2-20 | H | Cl | $OCH_2C\equiv CH$ |

The production examples of the pyridazin-3-one compounds given in the formula (I) from the present compounds are described as reference examples 2 below.

Reference Example 2-1

Two mililiters (2 ml) of a mixture of sulfuric acid and water (v/v=1/1), and 0.5 g of 2-(4-chlorophenyl)-6-ethoxycarbonyl-5-trifluoromethylpyridazin-3-one (the present compound 1-51) were mixed and heated for 5 hours on a 150° C. oil bath. The reaction solution was cooled to room temperature, poured into water and extracted with 100 ml of ethyl acetate. The organic layer was washed with 50 ml of saturated sodium chloride solution twice and dried over anhydrous magnesium sulfate. The solvent was removed under reduced pressure and the obtained crystals were washed with 50 ml of n-hexane to afford 0.18 g of 2-(4-chlorophenyl)-5-trifluoromethylpyridazin-3-one (yield:45%).

$^1$H-NMR (CDCl$_3$/300 MHz); 7.30(1H,s), 7.46(2H,d), 7.59(2H,d), 8.04(1H,q)

Reference Example 2-2

Three mililiters (3 ml) of a mixture of sulfuric acid and water (v/v=2/1), and 1.5 g of 2-(4-chloro-2-fluoro-5-isopropoxyphenyl)-6-ethoxycarbonyl-4-methyl-5-trifluoromethylpyridazin-3-one (the present compound 1-31) were mixed and heated for 6 hours on a 130° C. oil bath. The reaction solution was cooled to room temperature, poured into 50 ml of water. The precipitated crystals were filtered off and washed with 50 ml of water twice. The crystals were dissolved with 100 ml of ethyl acetate and dried over anhydrous magnesium sulfate. The solvent was removed under reduced pressure and the obtained crystals were washed with 20 ml of n-hexane to afford 0.55 g of 2-(4-chloro-2-fluoro-5-hydroxyphenyl)-4methyl-5-trifluoromethylpyridazin-3-one (yield:50%).

Reference Example 2-3

A half gram (0.5 g) of 2-(4-chloro-2-fluoro-5-hydroxyphenyl)-6-ethoxycarbonyl-4-methyl-5-trifluoromethylpyridazin-3-one (the present compound 1-27) and 1.5 ml of a mixture of sulfuric acid and water (v/v=1/1) were mixed and heated for 5 hours on a 130° C. oil bath. The reaction solution was cooled to room temperature, allowed to stand at the same temperature overnight, and further heated for 8 hours on a 130° C. oil bath. The reaction solution was cooled to room temperature and poured into 50 ml of water. The precipitated crystals were filtered off, dissolved with 100 ml of ethyl acetate, dried over anhydrous magnesium sulfate and treated with active charcoal. The solvent was removed under reduced pressure to afford 0.21 g of 2-(4-chloro-2-fluoro-5-hydroxyphenyl)-4-methyl-5-trifluoromethylpyridazin-3-one (yield:51%).

Reference Example 2-4

Twenty mililiters (20 ml) of a mixture of sulfuric acid and water (v/v=1/1), and 7.3 g of 2-(4-chloro-3-isopropoxycarbonylphenyl)-6-ethoxycarbonyl-4-methyl-5-trifluoromethylpyridazin-3-one (the present compound 1-109) were mixed and heated for 7 hours on a 150° C. oil bath. The reaction solution was cooled to room temperature, poured into 100 ml of water. The precipitated crystals were filtered off, washed with 50 ml of water 3 times, dissolved with 200 ml of ethyl acetate and dried over anhydrous magnesium sulfate. The solvent was removed under reduced pressure to afford 4.88 g of 2-(4-chloro-5-carboxyphenyl)-4-methyl-5-trifluoromethylpyridazin-3-one (yield:89%).

$^1$H-NMR (CDCl$_3$/300 MHz); 2.44(3H,q), 7.60(1H,d), 7.82(1H,dd), 8.04(1H,s), 8.34(1H,d)

What is claimed is:

1. A 6-alkoxypyridazin-3-one compound given in the formula:

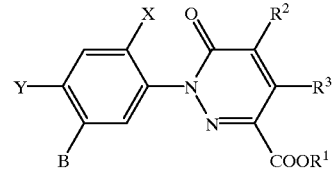

wherein, X represents a hydrogen or halogen atom; Y represents a halogen atom; $R^1$ represents a $C_1$–$C_6$ alkyl group; $R^2$ represents a hydrogen atom or $C_1$–$C_3$ alkyl group; $R^3$ represents a $C_1$–$C_3$ haloalkyl group; B represents a hydrogen atom, $OR^4$ group or $COOR^5$ group; $R^4$ represents a hydrogen atom, $C_1$–$C_6$ alkyl, $C_3$–$C_6$ alkenyl, $C_3$–$C_6$ alkynyl, ($C_1$–$C_8$ alkoxy)carbonyl$C_1$–$C_6$ alkyl or carboxy$C_1$–$C_6$ alkyl group; and $R^5$ represents a hydrogen atom, $C_1$–$C_6$ alkyl, $C_3$–$C_6$ alkenyl or $C_3$–$C_6$ alkynyl group.

2. The 6-alkoxycarbonylpyridazin-3-one compound according to claim 1, wherein $R^3$ is trifluoromethyl group.

3. A method of producing the pyridazin-3-one compounds given in the formula:

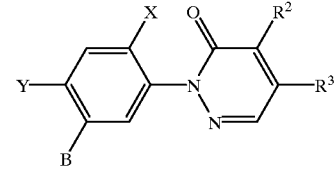

wherein, X represents a hydrogen or halogen atom; Y represents a halogen atom; $R^2$ represents a hydrogen atom or $C_1$–$C_3$ alkyl group; $R^3$ represents a $C_1$–$C_3$ haloalkyl group; B represents a hydrogen atom, $OR^4$ group or $COOR^5$ group;

$R^4$ represents a hydrogen atom, $C_1$–$C_6$ alkyl, $C_3$–$C_6$ alkenyl, $C_3$–$C_6$ alkynyl, ($C_1$–$C_8$ alkoxy)carbonyl$C_1$–$C_6$ alkyl or carboxy$C_1$–$C_6$ alkyl group;

and $R^5$ represents a hydrogen atom, $C_1$–$C_6$ alkyl, $C_3$–$C_6$ alkenyl or $C_3$–$C_6$ alkynyl group, which comprises i) reacting the hydrazone compound of the formula (III):

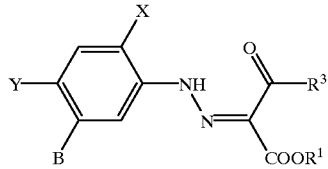

wherein, X, Y, B and $R^3$ represent the same definitions as above and $R^1$ represents a $C_1$–$C_6$ alkyl group, with the phosphorane compound given in the formula:

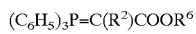

$(C_6H_5)_3P=C(R^2)COOR^6$ wherein, $R^2$ represents the same definition as above and $R^6$ represents a $C_1$–$C_6$ alkyl group, to obtain the 6-alkoxycarbonylpyridazin-3-one compounds given in the formula:

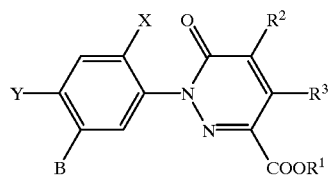

wherein, X, Y, B, $R^1$, $R^2$ and $R^3$ represent the same definitions as above and ii) treating the obtained 6-alkoxycarbonylpyridazin-3-one compounds with an acid.

4. The process according to claim 3, wherein step (ii) is carried out at a temperature between room temperature and 250° C.

5. The process according to claim 4, wherein step (ii) is carried out at a temperature between 50° C. and 200° C.

* * * * *